United States Patent
Hassell et al.

(10) Patent No.: US 12,222,279 B2
(45) Date of Patent: Feb. 11, 2025

(54) FLOW CELL DEVICE AND BIOREACTOR PRODUCT MONITORING SYSTEM AND METHOD

(71) Applicant: Nirrin Technologies, Inc., Billerica, MA (US)

(72) Inventors: Bryan A. Hassell, Cambridge, MA (US); Aaron Delahanty, Freeville, NY (US)

(73) Assignee: Nirrin Technologies, Inc., Billerica, MA (US)

( * ) Notice: Subject to any disclaimer, the term of this patent is extended or adjusted under 35 U.S.C. 154(b) by 52 days.

(21) Appl. No.: 16/751,895

(22) Filed: Jan. 24, 2020

(65) Prior Publication Data
US 2020/0240902 A1    Jul. 30, 2020

Related U.S. Application Data

(60) Provisional application No. 62/796,400, filed on Jan. 24, 2019.

(51) Int. Cl.
*G01N 21/03* (2006.01)
*B01L 3/00* (2006.01)
(Continued)

(52) U.S. Cl.
CPC .......... *G01N 21/0332* (2013.01); *B01L 3/502* (2013.01); *C12M 47/20* (2013.01);
(Continued)

(58) Field of Classification Search
CPC .............. G01N 21/0332; G01N 21/05; G01N 2021/0389; G01N 21/3577; G01N 21/359; B01L 3/502; B01L 2200/0689; B01L 2300/0663; B01L 2300/12; B01L 2300/1822; B01L 2400/082; C12M 47/20
(Continued)

(56) References Cited

U.S. PATENT DOCUMENTS 4,180,739 A * 12/1979 Abu-Shumays ... G01N 21/0332
                                                250/458.1
6,565,815 B1 *  5/2003 Chang ....................... B01L 7/52
                                                422/417
(Continued)

FOREIGN PATENT DOCUMENTS

EP        1181098        7/2006

OTHER PUBLICATIONS

International Search Report and Written Opinion of the International Searching Authority, mailed on May 6, 2020, from International Application No. PCT/US2020/014964, filed on Jan. 24, 2020. 19 pages.
(Continued)

*Primary Examiner* — Jill A Warden
*Assistant Examiner* — Jacqueline Brazin
(74) *Attorney, Agent, or Firm* — HoustonHogle LLP

(57) ABSTRACT

A flowcell device, including a flow pathway and an optical subassembly, has a flowcell body that is continuous with a sample being analyzed and a temperature controlled surface. The flowcell body can be disposed between a thermalplate, actively regulated by a thermoelectric cooler, and an insulating member. The flowcell device can be employed in a bioreactor monitoring system.

20 Claims, 7 Drawing Sheets

(51) Int. Cl.
*C12M 1/00* (2006.01)
*G01N 21/05* (2006.01)

(52) U.S. Cl.
CPC ...... *G01N 21/05* (2013.01); *B01L 2200/0689* (2013.01); *B01L 2300/0663* (2013.01); *B01L 2300/12* (2013.01); *B01L 2300/1822* (2013.01); *B01L 2400/082* (2013.01); *G01N 2021/0389* (2013.01)

(58) Field of Classification Search
USPC ...................................................... 422/82.05
See application file for complete search history.

(56) References Cited

U.S. PATENT DOCUMENTS

| | | | |
|---|---|---|---|
| 9,146,189 B2 | 9/2015 | Koerperick et al. | |
| 9,540,701 B2 | 1/2017 | Olesberg et al. | |
| 2004/0200909 A1* | 10/2004 | McMillan | B01L 7/52 241/1 |
| 2010/0087325 A1* | 4/2010 | Buermann | C40B 60/12 506/7 |
| 2010/0265492 A1* | 10/2010 | Schroeder | G01N 33/2823 356/51 |
| 2019/0358632 A1 | 11/2019 | Hassell et al. | |

OTHER PUBLICATIONS

International Preliminary Report on Patentability mailed on Aug. 5, 2021, from International Application No. PCT/US2020/014964, filed on Jan. 24, 2020. 13 pages.

Davies, A.M.C., "An Introduction to Near Infrared (NIR) Spectroscopy", 1-5 (2017). http://www.impublications.com/content/introduction-near-infrared-nir-spectroscopy.

Cervera, A. E., et al., "Application of near-infrared spectroscopy for monitoring and control of cell culture and fermentation," Biotechnol. Prog., 25(6): 1561-1581 (2009).

Roggo, Y., et al., "A review of near infrared spectroscopy and chemometrics in pharmaceutical technologies," Journal of Pharmaceutical and Biomedical Analysis, 44(3): 683-700 (2007).

* cited by examiner

FLOW CELL DEVICE AND BIOREACTOR PRODUCT MONITORING SYSTEM AND METHOD

RELATED APPLICATIONS

This application claims the benefit under 35 USC 119(e) of U.S. Provisional Application No. 62/796,400, filed on Jan. 24, 2019, which is incorporated herein by reference in its entirety.

BACKGROUND OF THE INVENTION

A number of different optical spectroscopy techniques exist. Probably the most common is absorption spectroscopy. Incident light excites electrons of the analyte from a low energy ground state into a high energy, excited state, and the energy can be absorbed by both non-bonding n-electrons and π-electrons within a molecular orbital. This analysis can be performed in the ultraviolet, visible, and/or infrared. Another option is Raman spectroscopy, which works by the detection of inelastic scattering of typically monochromatic light from a laser.

In absorption spectroscopy, analytes of varying material phases and composition are interrogated by specific wavelengths or wavelength bands of light, the resulting transmitted light can be used to resolve the absorbed spectra. Absorbed spectra may be used to determine the analyte's or sample's composition, temperature, pH and/or other intrinsic properties for applications ranging from medical diagnostics, pharmaceutical development, food to beverage quality control, to list a few examples.

SUMMARY OF THE INVENTION

Devices have been developed to meter, contain, and interrogate analytes in a sample. However, the quality of emitted and/or absorbed spectra can vary based on a number of variables, e.g. temperature. In order to facilitate adoption of these techniques a manufacturable, robust device that is capable of withstanding repeated sterilization protocols and features an ability for highly precise modulation of sample temperatures would be desirable. Also desirable are hands-free, non-destructive, real time techniques for identifying and/or quantifying constituents in a given process, such as, for instance, a process conducted in a vessel, e.g., a bioreactor.

The present invention generally relates to opto-fluidic devices, and techniques for temperature regulation and the use of such devices. The subject matter of the present invention involves, in some cases, interrelated products, alternative solutions to set of problems, and/or a different uses of one or more systems and/or articles.

In one aspect, the present invention is generally directed to an optofluidic apparatus, herein referred to as a "flowcell". In one set of embodiments, the flowcell has a first fluid channel defined within a flow cell body; a second fluid channel defined within the body extending substantially parallel to the first. A central cell, through which light passes, is in fluid communication with the first fluid channel and the second fluid channel.

The flow cell body is thermally continuous with both the analytical sample and a temperature-controlled surface. The central cell (through which light passes) is defined within the flowcell's body and by adjacent optical windows. Furthermore, the optical windows and central cell are sealed from the external environment by means of chemical-resistant sealing gaskets and a rigid, temperature insulating body, facilitating compression of the sealing material.

Preferably, the flowcell is used as part of a fluidic system that enables optical interrogation with thermal control. The flowcell is situated substantially parallel and in positive force contact with a thermal plate; a thermoelectric cooler (TEC) is bonded to the thermal plate such that the active surface of the TEC is in thermal communication with the flowcell's central body and thus the fluid sample contained within. The passive surface of the TEC is thermally bonded to a heatsink through which active convection heat transfer brings the passive surface of the TEC towards ambient air temperature. The component serving as the TEC heatsink can also position the optical collimator which is aligned to transmit electromagnetic energy from an optical source through the central cell and ultimately into an optical detector.

In another aspect, the present invention is generally directed to a method of optical interrogation in which the flowrate and temperature of the fluid samples from a bioreactor, for example, are independently controlled by a common digital controller. As fluid samples are brought into the flowcell, they begin to equilibrate to temperature at which the flowcell is actively being regulated (here 23 C+/−0.1 C), the flow is then fully occluded, allowing the sample to come to rest. Multiple optical interrogations, will, over time, result in spectra that converge to a stable spectrum as the flowcell and the sample in the central cell come to a temperature equilibrium, at which time a final spectrum can be obtained before re-initiating flow and repeating the process. Specific implementations rely on near infrared (NIR) absorption spectrometry techniques.

Embodiments described herein can be practiced to address spectral fluctuations caused by changes in temperature or to locally and quickly control the temperature of a fluid in a flow cell. In some implementations, the invention adds temperature control capabilities in a flow system designed to analyze the contents of a bioreactor. The analysis can be conducted in real time, in a nondestructive manner, and the sample can be returned to the bioreactor once the analysis is completed.

Some implementations utilize detachable parts that can be assembled and disassembled as needed, offering flexibility and convenience. In some cases, some, most or all the detachable parts can withstand autoclave operations. Disposable components, if used, can simplify and speed up the analysis process.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a scale front plan view, FIG. 2 is a scale side cross sectional view taken along line C-C of FIG. 1, FIG. 3 is a detailed side cross sectional view of area D of FIG. 2, FIG. 4 is a side exploded view of the flowcell device, and FIG. 5 is a perspective exploded view of the flowcell device.

DETAILED DESCRIPTION OF THE PREFERRED EMBODIMENTS

Figure 1:
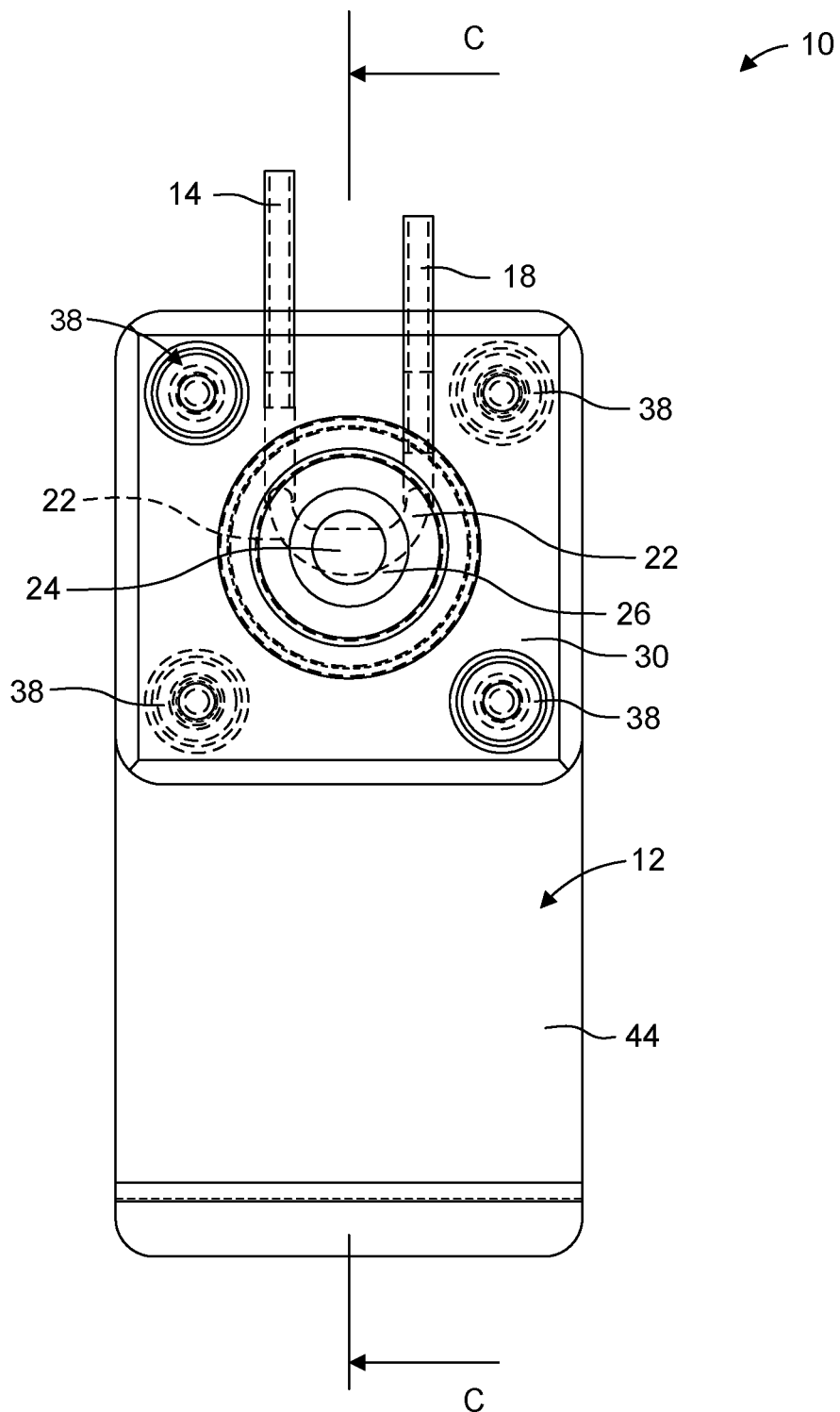
FIGS. 1-5 show a flowcell device according to embodiments of the present invention.
Figure 2:
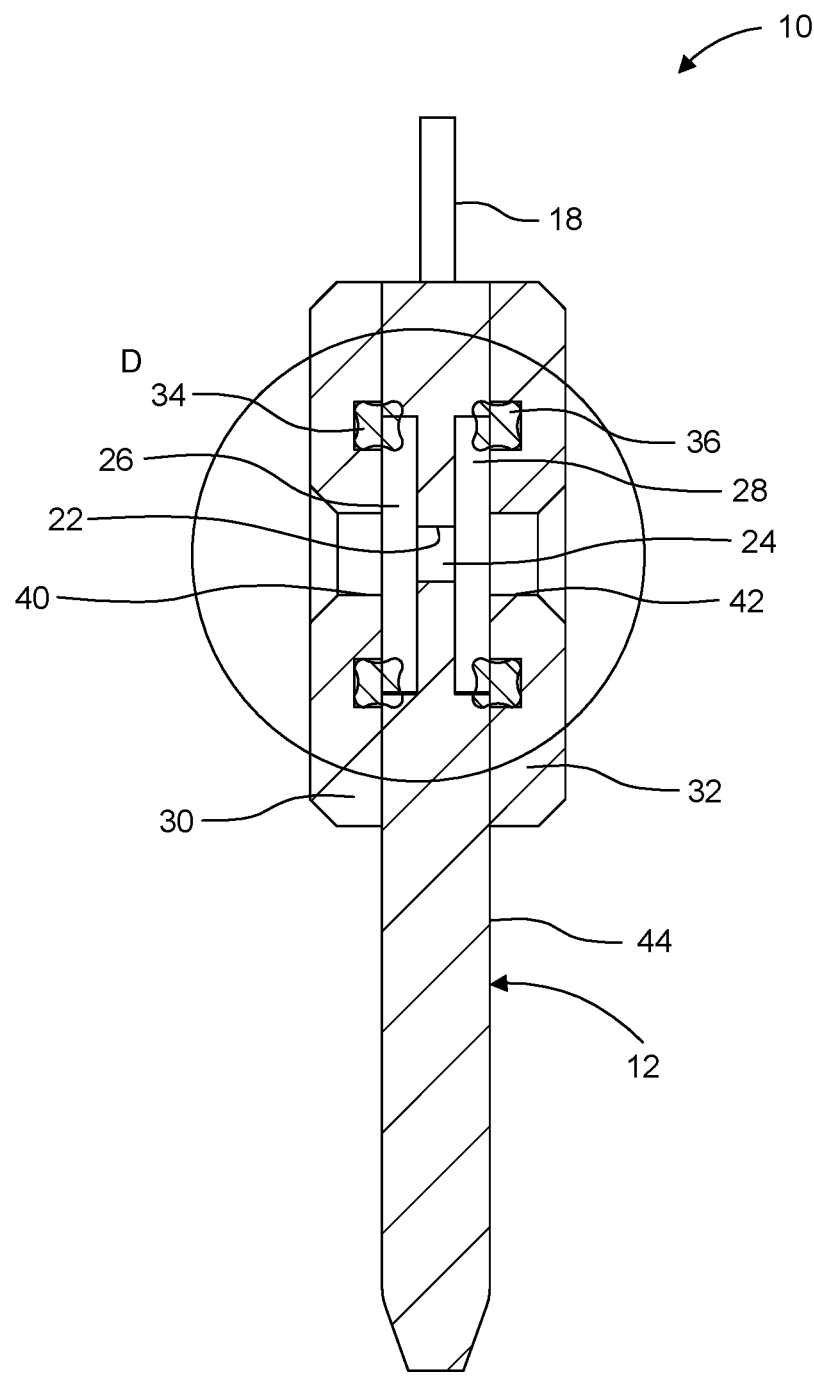
Figure 3:
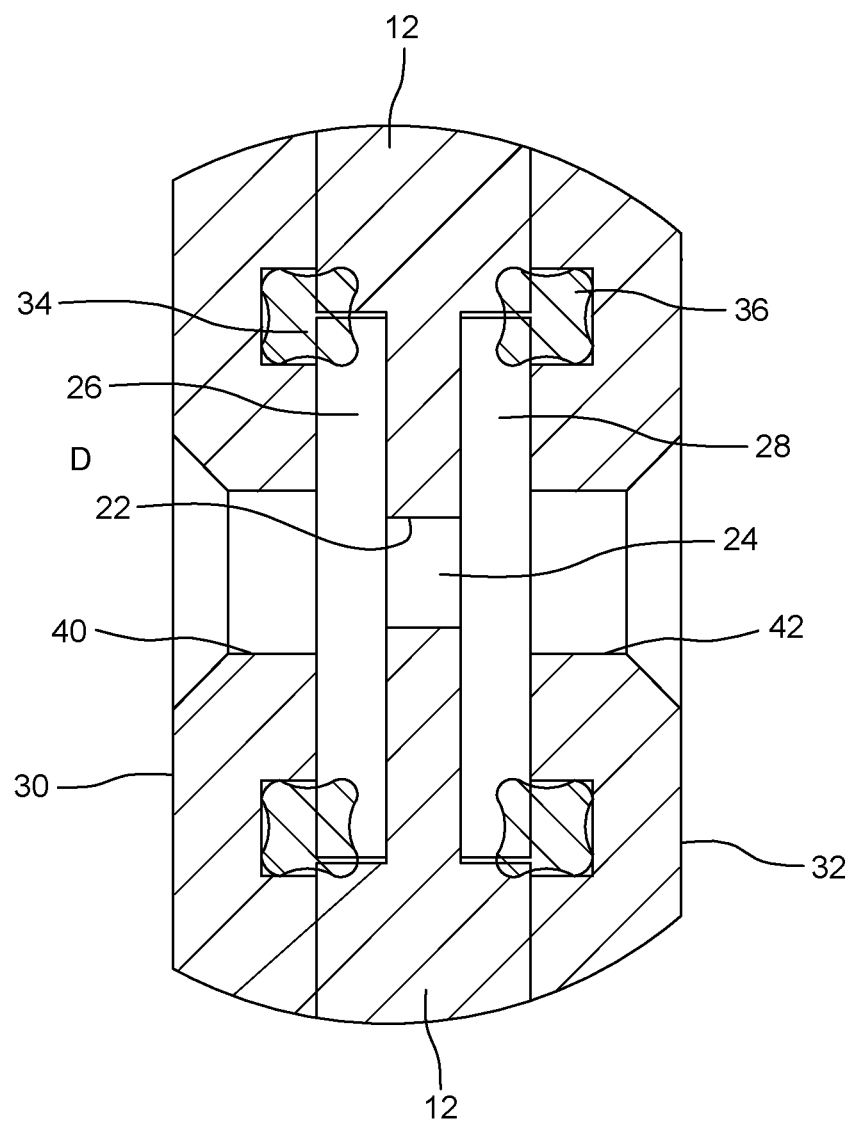
Figure 4:
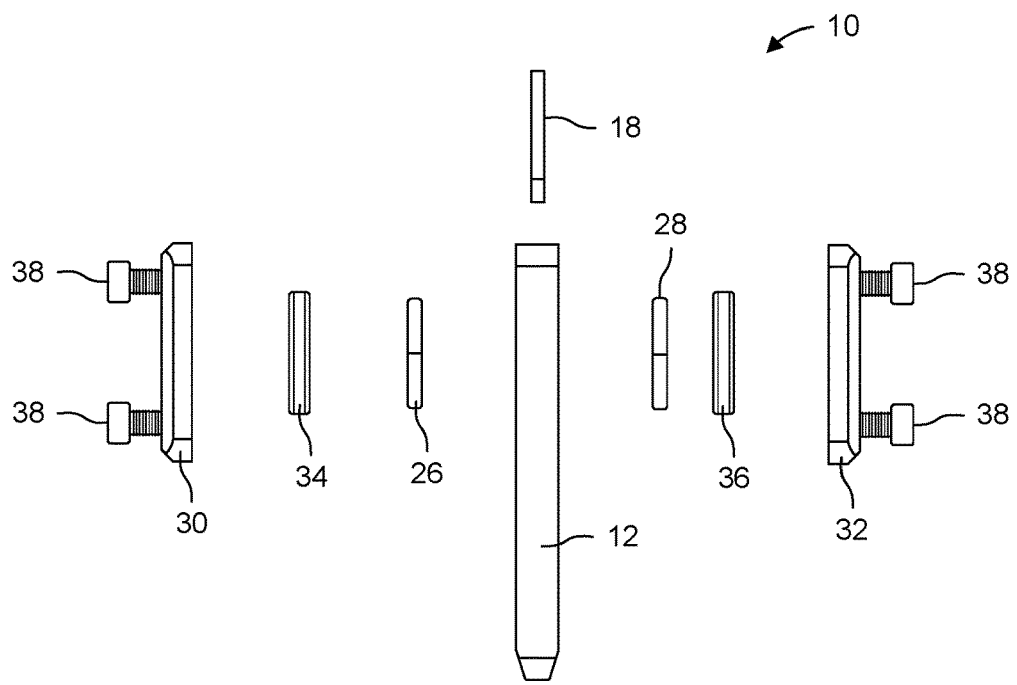
Figure 5:
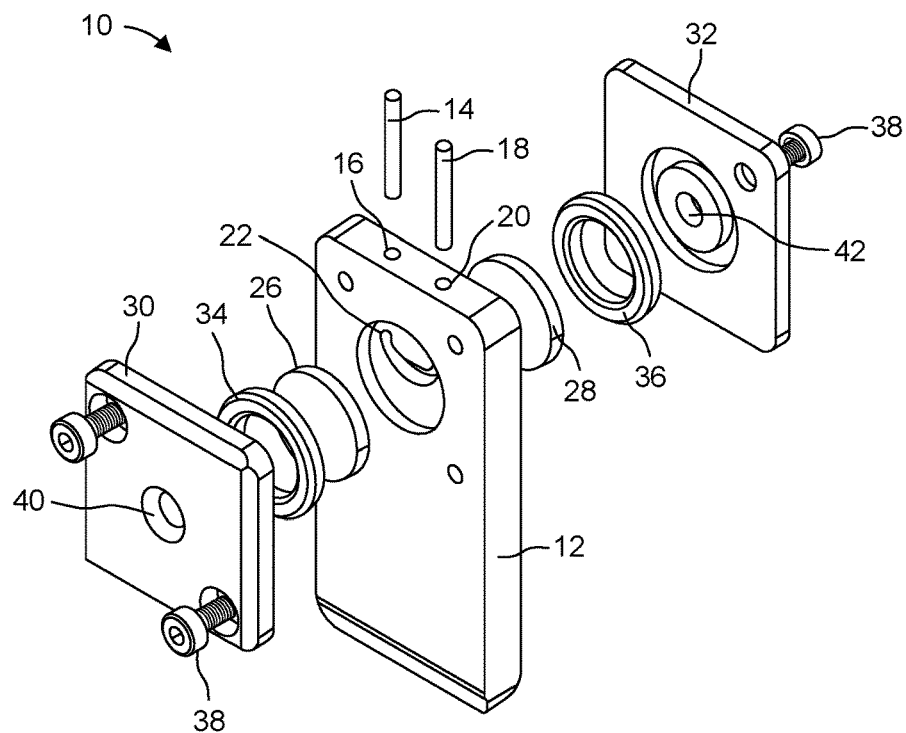

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention generally relates to techniques and equipment for analyzing samples that may contain cells, culture media, nutrients, metabolites, enzymes, hormones, cytokines and so forth. One use, for example, is the determination of glucose and/or lactic acid concentration in the fluid contained in the bioreactor. In many cases, the samples are withdrawn from and returned to a bioreactor.

Some implementations described herein rely on near infrared (NIR) spectroscopy. Probing molecular overtone and combination vibrations, NIR spectroscopy covers the region of from 780 nanometer (nm) to 2500 nm of the electromagnetic spectrum. An overview of NIR spectroscopy can be found, for example, in an article by A. M. C. Davies in "An Introduction to Near Infrared (NIR) Spectroscopy", http://www.impublications.com/content/introduction-near-infrared-nir-spectroscopy. See also, Cervera, A. E., Petersen, N., Lantz, A. E., Larsen, A. & Gernaey, K. V. Application of near-infrared spectroscopy for monitoring and control of cell culture and fermentation, Biotechnol. Prog. 25, 1561-1581 (2009); and Roggo Y, et al., "A review of near infrared spectroscopy and chemometrics in pharmaceutical technologies", Journal of Pharmaceutical and Biomedical Analysis, Volume 44, Issue 3, 2007.

Among its strength, NIR spectroscopy presents a non-invasive, non-destructive investigative approach, typically involving fast scan times. A discussion of NIR as applied to microfluidic and other systems is provided in U.S. patent application Ser. No. 16/419,690, to Hassell et al., filed on May 22, 2019 and incorporated herein in its entirety by this reference.

Equipment and/or techniques described herein can be applied or adapted to other spectroscopic analysis methods.

In many of its aspects, the invention relates to a flow cell device configured for controlling the temperature of a sample being analyzed. The device can be thought to include a fluid flow component or subassembly and an optical component or subassembly. In many arrangements, the direction of the sample flow through a cell used to conduct the spectroscopic analysis is orthogonal to the light pathway in the optical subassembly.

FIGS. 1-5 show a flow cell device 10 constructed according to the principles of the present invention.

Generally, the flowcell device 10 includes a flowcell body 12. Preferably the body is constructed from a rigid material that is thermally conductive and is relatively inert with respect to the sample or analyte. Possible materials include stainless steel, aluminum or diamond, for example.

A sample containing one or more analytes is received through a first (inlet) fluid channel, which is defined by a stainless steel tube 14 that is inserted into a port 16 that has been machined into the flow cell body 12. The sample then passes out through a second (outlet) fluid channel, which is defined by another stainless steel tube 18 that is inserted into another port 20 that has been machined into the flow cell body.

These tubes can be press fit, thermal press fit, can use threaded connections, and/or can employ epoxy bonding to the flow cell body.

Other embodiments may feature multiple inlets, with a single outlet, multiple outlets with a single inlet, or some combination of multiple inlets and multiple outlets.

A "U" shaped channel 22 within the flowcell body connects the first fluid channel 14 to the second fluid channel 18. The central cell 24, for conducting the sample analysis, and also referred to herein as the "sample" cell is located at the belly or lowest section of this "U" shaped channel 22.

In the illustrated embodiment, a simple "U" shape' channel is shown. However, this geometry may be altered to suit specific microfluidic functions, such as a serpentine-mixing channel, or a channel designed to filter or sort a heterogenous fluid.

Generally, the "U" shaped channel 22 is defined on its lateral sides by the bulk of the flow cell body 12. Its front and back sides are defined by first and second optical windows, 26, 28, fabricated from a transmissive and inert material such as optical-grade transparent windows of fused silica, quartz, sapphire, borosilicate glass, Cyclic Olefin Polymer, Cyclic Olefin Copolymer, etc. Other materials, transparent to NIR, for example, can be employed.

The windows are sealed against the flow cell body with respective caps 30, 32, and gaskets 34, 36. The caps can be formed from polyetherimide (PEI), such as Ultem®, polyether ether ketone (PEEK), etc. and can be bolted to the flowcell body 12, or to each other through the body, to sandwich the flow cell body, gaskets and the two windows between them. For directing light through central cell 24, the caps are provided with optical ports 40, 42.

The optical-grade transparent windows are contained within the device by gaskets 34, 36, e.g., O-rings, such as X-profile O-rings (Vitron quadrings, for example) and The O-rings are compressed by fasteners (e.g., M2 socket head cap screws 38) to form a liquid tight seal. Leak testing could be conducted at atmospheric pressure under 0.5 ml/min flow for 24 hours).

From a suitable light source, light is transmitted through windows (26, 28) and a fluid sample in the central cell 24 such that the transmission and/or absorption and/or scattering can be measured by a light detector (here a photodiode or photo multiplier tube, CMOS, CCD detector, etc.).

Heating or cooling can be applied at one or more suitable points of the flow cell body 12, the thermal conductivity of the material used to construct the flow cell body ensuring that the sample being analyzed in central cell 24 is heated or cooled as desired. In some implementations, the flow cell body is continuous with a temperature-controlled surface. In one example, the flow cell body 12 includes a section 44, that can be heated via a thermal plate, as further described below. In the embodiments of FIGS. 1-5, this section 44 is underneath "U"-shaped channel 22 and central cell 24.

All components can be selected to withstand autoclave sterilization (249 degrees F.). Furthermore, the device can be fully disassembled (with exception of permanently bonded tubing and thermal core), such that components could be individually cleaned and/or replaced.

Figure 6:
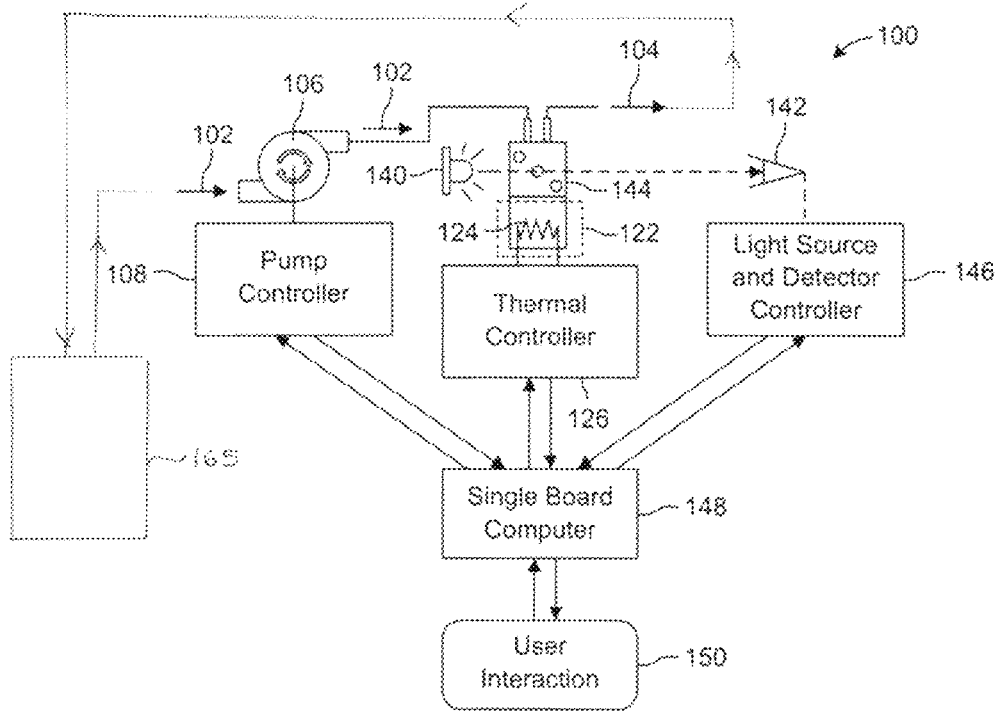
FIG. 6 is a block diagram showing a bioreactor monitoring system including a flowcell device configured to facilitate thermal control over the flowcell.

FIG. 6 illustrates a multi-component optofluidic system 100 including the flowcell device 10 and communication pathways to facilitate thermal control over the flowcell.

During operation, a sample is extracted from a bioreactor, directed to the flowcell device 10 (see arrow 102) and returned to the bioreactor 165 (arrow 104) once the analysis is completed. The fluid flow is driven be pump 106 (such as a peristaltic pump or another suitable device) controlled by pump controller 108. The flow can be stopped to retain a sample in central cell 24 for the time needed to reach a temperature equilibration and obtain a stabilized spectrum that can be stored.

System 100 also includes an arrangement 120, in which flowcell device 10 is physically placed between a thermally insulating member 122 that applies a clamping force and a thermalplate 124, that is actively temperature controlled by a thermal controller 126. Attached to thermalplate 124 is a thermoelectric cooler (TEC), such as a Peltier device (often constructed from thermally-conductive ceramic that uses the electrical power supplied by a temperature controller to cool one of its surfaces while heating the opposing surface). A fan can be added to enhance thermal performance.

The passive side of the TEC is in thermal contact with a large heatsink, through which active convective heat exchange is applied. Completing the loop, a thermistor temperature sensor is also permanently bonded and in thermal contact with the thermalplate to provide feedback control of the flowcell device's temperature. Often, the contents of the bioreactor are at a temperature within a range of from about 36 to about 38. The target temperature of the sample in the central cell 24 can be a desired temperature, e.g., an ambient room temperature.

The interrogating optical signal is generated by a tunable laser 140 and introduced to the optical subassembly through a collimator, which is aligned to the output of a photodiode unit 142 by means of three sets of precision alignment pins 144. In other cases, a broadband source such as a super luminescent light emitting diode (SLED) source could be used along with a spectrally resolving detector. Control of the light source and detector is provided by controller 146.

In one implementation, the system 100 is controlled by a single board computer 148 that receives the spectra from the light source 140 and detector controller 146, instructs the thermal controller 122 concerning the selected temperature at which the flowcell 10 is to be regulated to and also controls the pump controller 108 that circulates the sample through the flowcell device 12 from the bioreactor and then returns the sample back to the bioreactor, in one example. The system can further include a user interaction function 150.

Figure 7:
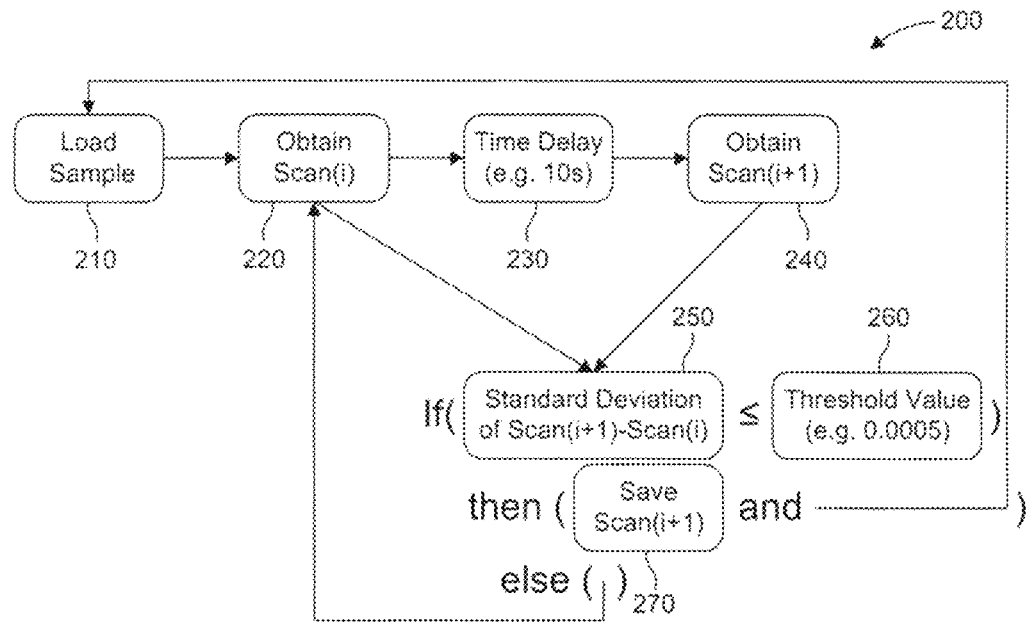
FIG. 7 is a process diagram showing the operation of the monitoring system and specifically how the computer captures and compares spectra.

FIG. 7 is a schematic diagram showing a control loop for acquiring spectra.

As shown in this diagram, multiple spectra are acquired (at suitable time intervals, e.g., every 10 seconds) and the standard deviation between them is calculated. If the standard deviation is at or below a certain threshold value, 0.0005 for example, then the spectra are saved and labeled as an equilibrated sample.

In more detail, protocol 200 begins with loading (step 210) a sample in a flowcell device such as described herein such as by operation of the pump 106. Once flow to and through the device is interrupted and the sample is retained in the central cell, scans, in the NIR region, for instance, can be taken sequentially, at a desired time interval. Each scan can be compared to the immediately preceding scan to determine a standard deviation between the two. For a standard deviation exceeding a targeted (threshold) standard deviation value, the scan is discarded and the process continues. As the sample temperature equilibrates, the scans become increasingly similar and the standard deviation between a scan and the immediately preceding scan reaches or falls below the threshold standard deviation value, at which point the scan is saved as a stable scan. For instance, in the illustration of FIG. 7, the sample is scanned in step 220, to obtain scan (i). The sample is allowed to equilibrate (230) for a desired time delay, e.g., 10 seconds, after which another scan (i+1) is obtained in step 240. The scans obtained in steps 220 and 240 are compared to obtain a standard deviation 250, which can be greater, equal to or smaller than a threshold standard deviation value 260.

If the samples are characterized by sequential spectra with a standard deviation that is greater than the threshold standard deviation, the computer instructs the pump controller to wait and not flush the current sample from the flowcell device, and the computer continues to obtain spectra until it determines that the spectra have stabilized (i.e., the standard deviation between scan (i+1) and scan (i) is equal to or less than the threshold standard deviation), at which time the current spectrum is recorded (step 270) and the computer instructs the pump controller to circulate the next sample into the flowcell device. As a process is being monitored over time, comparing saved spectra that correspond to temperature-stabilized samples circumvents measurement artifacts caused by temperature fluctuations.

Figure 8:
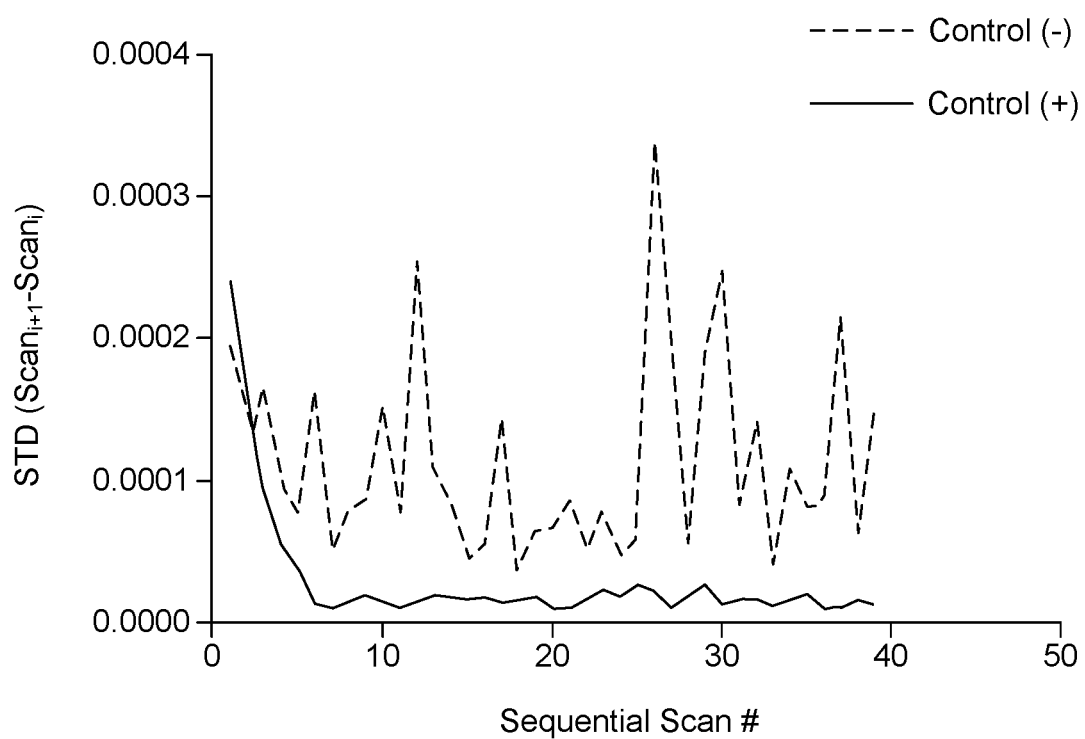
FIG. 8 is a plot of the standard deviation of spectra for a temperature controlled system and a system in which the temperature is unregulated.

FIG. 8 is a plot of the standard deviation of spectra for a temperature controlled system (solid line) and a system in which the temperature is unregulated (dashed line).

Figure 9:
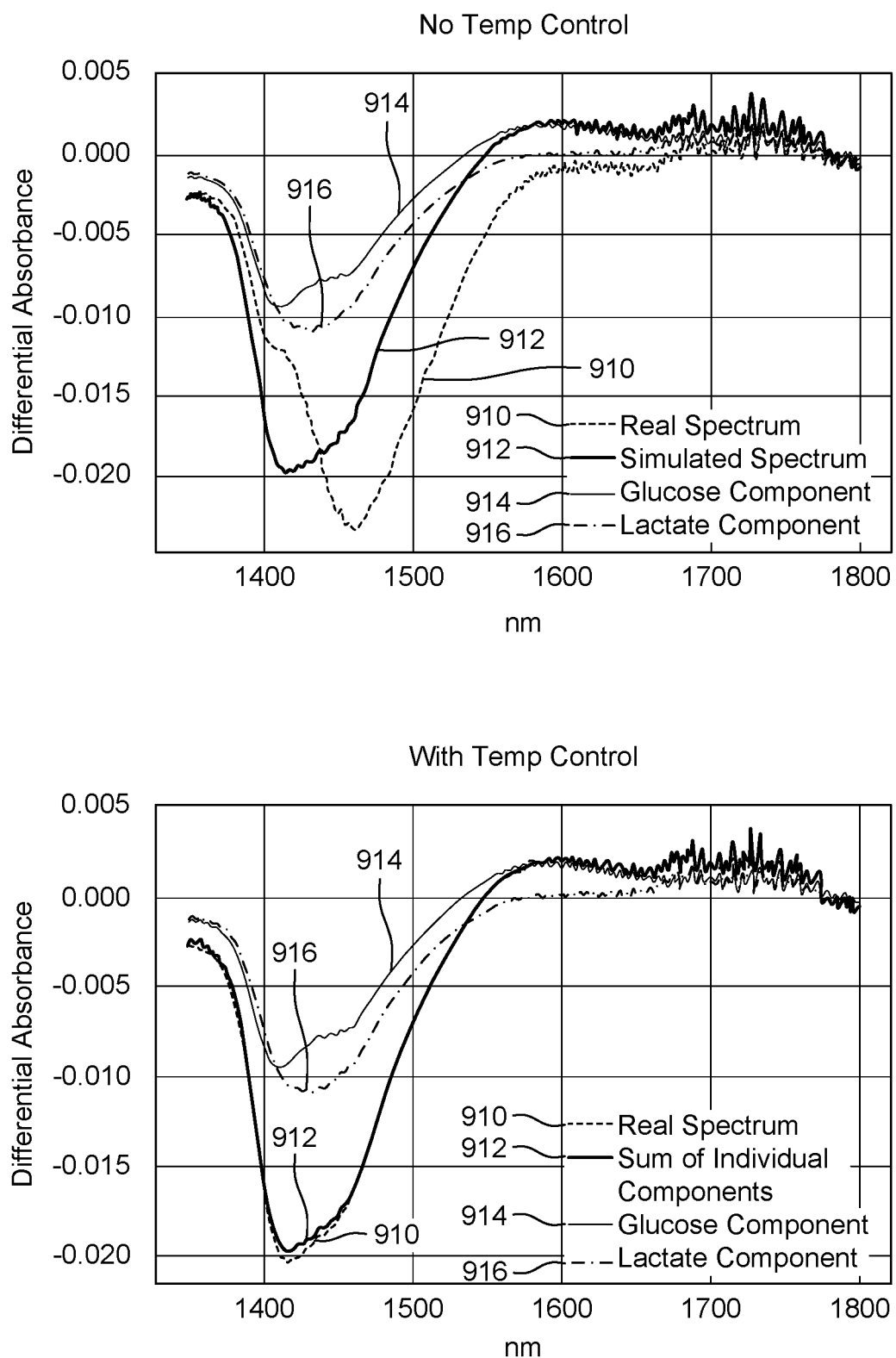
FIG. 9 compares plots of the differential absorbance with no temperature control and with control.

FIG. 9 compares plots of the differential absorbance with no temperature control and with control. In this experiment spectra were acquired of homogenous solutions of a mixture of glucose (see spectra 914) and lactate (see spectra 916) with and without temperature control. Through the use of Beers law and by the fact that the concentrations of the glucose and lactate are known, a simulated spectra can be generated that should agree with the actually acquired, real, spectra. Note the improved ability to simulate the spectra of the multicomponent mixture in the condition with temperature control by the alignment between the simulated spectrum (912) and the real spectrum (910). Spectra 914 is the glucose component and spectra 916 is the lactate component.

In initial tests, the system has demonstrated the ability to control temperatures between 15 degrees centigrade (° C.) and 40° C. when the system is in a room temperature environment. In further experiments, the flow cell has been regulated to 23+/−0.1° C. If the actively regulated and sensed surface falls outside of the tolerance window a signal is sent to alert the control system and discard the scan.

In other embodiments, the system actively sweeps temperature (e.g. from 23° C. to 40° C. at 1° C. increments) and acquires the NIR absorption of different analytes at different temperatures. This information may be useful in several different ways, including but not limited to model generation, model validation, temperature sensing in an unregulated environment. In some cases, obtaining spectra at the same temperature and at different stages of the process can be used to monitor the contents of the bioreactor as a function of time, to observe, for instance, the depletion of some ingredients and/or the appearance and increase of others.

Embodiments described herein can be practiced in downstream applications, for example at a stage at which a product (drug, for example) is collected from the bioreactor and thus not temperature controlled. Use of a flow cell device (including a flow cell and associated temperature components) can allow one to quickly and locally change and/or control the temperature of an incoming fluid for spectral scanning. Other applications include quality control of reactor product.

While this invention has been particularly shown and described with references to preferred embodiments thereof, it will be understood by those skilled in the art that various changes in form and details may be made therein without departing from the scope of the invention encompassed by the appended claims.

What is claimed is:

1. A flowcell device comprising:
    a light source;
    a flowcell body defining a flow pathway that includes a central cell;
    a thermal plate in thermal contact with the flowcell body;
    a Peltier device for controlling a temperature of the flowcell body via the thermal plate; and
    an optical subassembly, comprising the central cell and adjacent first and second optical windows and a light source and a detector for determining an absorption spectra of a sample in the central cell via the first and second optical windows,
    wherein, in the central cell, the flow pathway and a light pathway from a light source through the central cell are orthogonal to one another, and wherein the flow pathway comprises a U-shaped channel that includes the central cell.

2. The flowcell device of claim 1, wherein the flow pathway is formed of an input channel, an output channel and a channel comprising the central cell and connecting the input channel and the output channel.

3. The flowcell device of claim 2, wherein the channel connecting the input channel and the output channel is U shaped, having lateral sides defined by a bulk of the flow cell body and front and back sides defined, respectively, by the first optical window and the second optical window.

4. The flowcell device of claim 1, wherein the input channel and the output channel are defined by steel tubes.

5. The flowcell device of claim 1, wherein the central cell contains a sample extracted from a bioreactor.

6. The flowcell device of claim 1, wherein the optical windows are sealed against the flow cell body by gaskets and caps.

7. The flowcell device of claim 1, wherein the flow cell body is fabricated from a rigid, thermally conductive material.

8. The flowcell device of claim 1, wherein one or more parts are autoclavable.

9. The assembly of claim 1, wherein an active surface of the Peltier device is in thermal communication with the flowcell body.

10. The assembly of claim 9, wherein a passive surface of the Peltier device is in thermal contact with a heat sink.

11. An assembly comprising:
    a bioreactor containing cells and a culture media;
    an actively temperature-controlled thermal plate;
    an optical source;
    an optical detector;
    a flowcell device having a flow cell body defining a channel that includes a central cell;
    a pump and a connector, whereby the sample is flowed from the bioreactor by the pump through the connector to the channel that includes the central cell, whereby the pump, the connector, and the channel that includes the central cell are fluidically connected;
    wherein the flowcell body has an optical subassembly, comprising the central cell and adjacent first and second optical windows,
    wherein the flowcell body is held between an insulating member and the actively temperature-controlled thermal plate while an absorption spectra of the sample is acquired using the optical source and the optical detector.

12. The assembly of claim 11, wherein the thermal plate is actively temperature controlled by a thermal controller including a thermoelectric cooler, a passive side of the thermoelectric cooler being in contact with a heat sink.

13. The assembly of claim 11, further comprising a sensor at the thermal plate.

14. An optofluidic system, comprising:
    a flowcell device having a flowcell body defining a flow pathway that includes a channel comprising a central cell;
    a bioreactor containing cells and a culture media;
    a pump and a connector, whereby the sample is flowed from the bioreactor with the pump through the connector to the channel comprising the central cell, whereby the pump, the connector, and the channel comprising the central cell are fluidically connected;

an optical subassembly, comprising the central cell, a first optical window and a second optical window;

a light source for directing light through the first optical window, the central cell and the second optical window;

an optical signal detector;

a thermal plate in contact with the flowcell body and supporting a thermoelectric cooler;

a thermal controller;

a sample flow controller;

a light source controller and/or detector controller; and a computer configured for controlling the thermal controller, the sample flow controller and the light source and/or detector controller, wherein the computer is configured for instructing the thermal controller to maintain a temperature of the sample in the flow cell device while acquiring an absorption spectra of the sample using the light source and the optical signal detector.

15. The optofluidic system of claim 14, further comprising a conduit to direct a sample from a bioreactor to the flowcell device and a conduit to direct the sample from the flowcell device to the bioreactor.

16. The optofluidic system of claim 14, wherein a sample flow and a flowcell temperature are independently controlled.

17. The optofluidic system of claim 14, wherein the computer is configured to regulate a temperature of a flowcell device via the thermal controller while flowing a sample through the flowcell device via the flow controller to obtain absorption spectra of the sample.

18. The optofluidic system of claim 17, configured for a standard deviation between a stable scan and a scan immediately preceding that is no greater than a threshold standard deviation value.

19. The optofluidic system of claim 17, configured for controlling the temperature within a range of from about 15 to about 40 degrees centigrade.

20. The flowcell device of claim 1, wherein the light source is a tunable laser.

* * * * *